United States Patent
Spannhoff et al.

(10) Patent No.: US 10,213,773 B2
(45) Date of Patent: *Feb. 26, 2019

(54) PROCESS FOR THE CONVERSION OF OXYGENATES TO OLEFINS

(71) Applicant: BASF SE, Ludwigshafen (DE)

(72) Inventors: Kirsten Spannhoff, Mannheim (DE); Florina Corina Patcas, Ludwigshafen (DE); Ekkehard Schwab, Neustadt (DE); Alexander Weck, Freinsheim (DE); Kerem Bay, Ludwigshafen (DE)

(73) Assignee: BASF SE (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/183,506

(22) Filed: Jun. 15, 2016

(65) Prior Publication Data

US 2016/0296923 A1  Oct. 13, 2016

Related U.S. Application Data

(63) Continuation of application No. 13/927,718, filed on Jun. 26, 2013.

(60) Provisional application No. 61/665,923, filed on Jun. 29, 2012.

(51) Int. Cl.
| | | |
|---|---|---|
| C07C 1/20 | (2006.01) |
| B01J 29/40 | (2006.01) |
| B01J 29/70 | (2006.01) |
| C07C 1/22 | (2006.01) |
| B01J 38/04 | (2006.01) |
| B01J 38/02 | (2006.01) |
| B01J 23/02 | (2006.01) |
| B01J 23/10 | (2006.01) |
| B01J 29/80 | (2006.01) |
| B01J 29/90 | (2006.01) |
| B01J 35/04 | (2006.01) |
| B01J 37/02 | (2006.01) |
| B01J 19/24 | (2006.01) |
| B01J 37/08 | (2006.01) |

(52) U.S. Cl.
CPC .......... *B01J 29/40* (2013.01); *B01J 19/2485* (2013.01); *B01J 23/02* (2013.01); *B01J 23/10* (2013.01); *B01J 29/70* (2013.01); *B01J 29/7038* (2013.01); *B01J 29/7049* (2013.01); *B01J 29/7088* (2013.01); *B01J 29/80* (2013.01); *B01J 29/90* (2013.01); *B01J 35/04* (2013.01); *B01J 37/0215* (2013.01); *B01J 37/0236* (2013.01); *B01J 37/08* (2013.01); *B01J 38/02* (2013.01); *B01J 38/04* (2013.01); *C07C 1/20* (2013.01); *C07C 1/22* (2013.01); *B01J 2219/2404* (2013.01); *B01J 2219/2434* (2013.01); *B01J 2219/2438* (2013.01); *B01J 2219/2446* (2013.01); *C07C 2523/78* (2013.01); *C07C 2529/40* (2013.01); *Y02P 20/584* (2015.11); *Y02P 30/42* (2015.11)

(58) Field of Classification Search
CPC ......... C07C 1/22; C07C 1/20; C07C 2529/40; B01J 38/02; B01J 38/04
USPC .... 502/527.19, 527.24, 34, 38, 56; 585/638, 585/639, 640
See application file for complete search history.

(56) References Cited

U.S. PATENT DOCUMENTS

| | | |
|---|---|---|
| 4,049,573 A | 9/1977 | Kaeding |
| 4,357,264 A | 11/1982 | Chu |
| 4,401,637 A | 8/1983 | Marosi et al. |
| 4,423,266 A | 12/1983 | Young |
| 4,433,189 A | 2/1984 | Young |
| 4,447,666 A | 5/1984 | McWilliams |
| 4,456,582 A | 6/1984 | Marosi et al. |
| 4,504,690 A | 3/1985 | Forbus et al. |
| 4,548,914 A | 10/1985 | Chu |
| 4,654,455 A | 3/1987 | Chao |
| 4,692,423 A | 9/1987 | Caesar |
| 5,993,642 A | 11/1999 | Mohr et al. |
| 6,046,373 A | 4/2000 | Sun |
| 2002/0038775 A1 | 4/2002 | Sterte et al. |
| 2007/0149384 A1 | 6/2007 | Ghosh et al. |
| 2009/0048093 A1 | 2/2009 | Mizutani et al. |
| 2010/0168492 A1* | 7/2010 | Inaki ................ B01J 23/02 585/639 |
| 2010/0217054 A1 | 8/2010 | Ito et al. |
| 2012/0116143 A1 | 5/2012 | Okita et al. |
| 2013/0197288 A1 | 8/2013 | Schafer et al. |
| 2014/0005456 A1 | 1/2014 | Spannhoff et al. |

(Continued)

FOREIGN PATENT DOCUMENTS

| | | |
|---|---|---|
| DE | 238733 A1 | 9/1986 |
| EP | 0007081 A1 | 1/1980 |

(Continued)

OTHER PUBLICATIONS

Zampieri, "Develorpment of MFI-type Zeolite Coatings on SiSiC Ceramic Monoliths for Catalytic Applications", Thesis 2007.*

(Continued)

*Primary Examiner* — Elizabeth D Wood
(74) *Attorney, Agent, or Firm* — Drinker Biddle & Reath LLP

(57) ABSTRACT

The present invention relates to a process for converting oxygenates to olefins, comprising
  (1) providing a gas stream comprising one or more ethers;
  (2) contacting the gas stream provided in (1) with a catalyst,
the catalyst comprising
  a support substrate and
  a layer applied to the substrate,
the layer comprising one or more zeolites of the MFI, MEL and/or MWW structure type.

21 Claims, No Drawings

(56) References Cited

U.S. PATENT DOCUMENTS

| | | |
|---|---|---|
| 2014/0005457 A1 | 1/2014 | Spannhoff et al. |
| 2014/0058180 A1 | 2/2014 | Klingelhöfer et al. |

FOREIGN PATENT DOCUMENTS

| | | |
|---|---|---|
| EP | 0034727 A2 | 9/1981 |
| EP | 2143700 A1 | 1/2010 |
| EP | 2446964 A1 | 5/2012 |
| JP | 2007137840 A | 6/2007 |
| RU | 2177468 C2 | 12/2001 |
| WO | WO-94/25151 A1 | 11/1994 |
| WO | WO-98/29519 A1 | 7/1998 |
| WO | WO-2007055357 A1 | 5/2007 |
| WO | WO-2009092779 A2 | 7/2009 |
| WO | WO-2010150676 A1 | 12/2010 |
| WO | WO-2011089263 A1 | 7/2011 |
| WO | WO-2012123556 A1 | 9/2012 |
| WO | WO-2012123557 A1 | 9/2012 |
| WO | WO-2012123558 A1 | 9/2012 |
| WO | WO-2013017497 A1 | 2/2013 |
| WO | WO-2014001410 A2 | 1/2014 |
| WO | WO-2014001411 A2 | 1/2014 |
| WO | WO-2014001412 A2 | 1/2014 |

OTHER PUBLICATIONS

Antia, J., et al., "Conversion of Methanol to Gasoline-Range Hydrocarbons in a ZSM-5 Coated Monolithic Reactior", Ind. Eng. Chem. Res., vol. 34, (1995) pp. 140-147.

Ciambelli, P., "Acid-Base Catalysis in The Conversion of Methanol to Olefins Over Mg-Modified Zsm-5 Zeolite", Successful Design of Catalysis, (1988), pp. 239-246.

Frieding, J., et al., "Extrusion of zeolites: Properties of catalysts with a novel aluminium phosphate sintermatrix", Applied Catalysis A: General, vol. 328, (2007), pp. 210-218.

Goryainova, T., et al., "Study of Magnesium-Containing Zeolite Catalysts for the Synthesis of Lower Olefins from Dimethyl Ether", Petroleum Chemistry, vol. 51, No. 3, (2011), pp. 169-173.

Hammon, U., et al., "Formation of Ethene and Propene from Methanol on Zeolite ZSM-5, II. Preparation of Finished Catalysts and Operation of a Fixed-Bed Pilot Plant", Applied Catalysis, vol. 37, (1998), pp. 155-174.

Ivanova S., et al., "ZSM-5 Coatings on β-SiC Monoliths: Possible New Structured Catalyst for the Methanol-to-Olefins Process", J. Phys. Chem. C, vol. 111, (2007), pp. 4368-4374.

Lee, Y., et al., "Novel aluminophosphate (AIPO) bound ZSM-5 extrudates with improved catalytic properties for methanol to propylene (MTP) reaction", Applied Catalysis A: General, vol. 374, (2010), pp. 18-25.

Lee, Y., et al., "Textural Properties and Catalytic Applications of ZSM-5 Monolith Foam for Methanol Conversion", Catal Lett, vol. 129, (2009), pp. 408-415.

McIntosh, R., et al., "The Properties of Magnesium and Zinc Oxide Treated ZSM-5 Catalysts for Conversion of Methanol Into Olefin-Rich Products", Applied Catalysis, vol. 6, (1983), pp. 307-314.

Okado, H., et al., "Deactivation Resistance of ZSM-5-Type Zeolites containing Alkaline Earth Metals used for Methanol Conversion", Applied Catalysis, vol. 41, (1988), pp. 121-135.

Patcas, F., et al., "The methanol-to-olefins conversion over zeolite-coated ceramic foams", Journal of Catalysis, vol. 231, (2005) pp. 194-200.

Yang, "Preparation of Modified ZSM-5/Cordierite Monolithic Catalyst and Their Catalytic Performance of Methanol to Olefin," Dissertation (2011), Executive Summary.

International Search Report for PCT/EP2013/063435, dated Jan. 8, 2014.

Japanese Office Action with English Translation for application 2015-519078, dated Jan. 24, 2017.

Japanese Office Action for Japanese Application No. 2015-519078, dated Oct. 17, 2017.

* cited by examiner

PROCESS FOR THE CONVERSION OF OXYGENATES TO OLEFINS

CROSS-REFERENCE TO RELATED APPLICATIONS

This application claims benefit under 35 U.S.C. § 120 of U.S. patent application Ser. No. 13/927,718 filed Jun. 26, 2013 which is now abandoned. U.S. patent application Ser. No. 13/927,718 which in turn claims benefit under 35 USC 119(e) of U.S. Provisional Application 61/665,923, filed Jul. 29, 2012, both applications of which are incorporated by reference in their entirety.

The present invention relates to a process for converting ethers to olefins using a catalyst in the form of a coated support substrate and using a catalyst for conversion of ethers to olefins which is obtainable according to the present invention.

INTRODUCTION

In view of increasing scarcity of mineral oil deposits which serve as starting material for preparation of lower hydrocarbons and derivatives thereof, alternative processes for preparing such commodity chemicals are becoming increasingly important. In alternative processes for obtaining lower hydrocarbons and derivatives thereof, specific catalysts are frequently used in order to obtain lower hydrocarbons and derivatives thereof, such as unsaturated lower hydrocarbons in particular, with maximum selectivity from other raw materials and/or chemicals. In this context, important processes include those in which methanol as a starting chemical is subjected to a catalytic conversion, which generally gives rise to a mixture of olefins, paraffins and aromatics.

In the case of such catalytic conversions, the challenge is to refine the catalysts used therein, and also the process regime and parameters thereof, in such a way that a few very specific products form with maximum selectivity in the catalytic conversion. Thus, these processes are named particularly according to the products which are obtained in the main. In the past few decades, particular significance has been gained by those processes which enable the conversion of methanol to olefins and are accordingly characterized as methanol-to-olefin processes (MTO process for methanol to olefins). For this purpose, there has been development particularly of catalysts and processes which convert methanol via the dimethyl ether intermediate to mixtures whose main constituents are ethene and propene.

Antia et al. in Ind. Eng. Chem. Res. 1995, 34, pages 140-147 describes the coating of a support substrate with ZSM-5 and the use thereof in a methanol-to-gasoline process (MTG process).

U.S. Pat. No. 4,692,423 relates to a process for preparing a supported zeolitic catalyst by applying a mixture of a zeolite in a polymerizable solvent, for example tetrahydrofuran, to a porous support substrate, and the latter may consist of organic or inorganic material.

Ivanova et al. in J. Phys. Chem. C 2007, 111, pages 4368-4374 relates to a foamed molding and to an extrudate composed of β-silicon carbide, to each of which a ZSM-5 coating is applied, and to the use of such a coated foam body and extrudate in methanol-to-olefin processes (MTO processes). Compared to the use of the pulverulent zeolite per se, an improvement in the catalytic activity/selectivity is observed here, the coated catalysts having a higher stability with respect to deactivation by coking.

Patcas, F. C. in Journal of Catalysis 2005, 231, pages 194-200, describes ceramic foams coated with ZSM-5 zeolite and the use thereof in methanol-to-olefin processes. More particularly, it is stated that, in comparison to zeolitic pellets, such coated ceramic foams should exhibit an improvement in activity and selectivity. At relatively low temperatures and relatively high space velocities, however, lower space-time yields are described compared to the zeolitic pellets.

WO 98/29519 A1 describes nonzeolitic molecular sieves and especially SAPO supported on inorganic materials, and the use thereof in methanol-to-olefin processes.

WO 94/25151 A1 describes zeolites and especially ZSM-5 supported on monoliths, and the use thereof as a molecular sieve in separation processes.

Hammon et al. in Applied Catalysis 1988, 37, pages 155-174 relates to processes for producing zeolite extrudates with little to no binder and the use thereof in methanol-to-olefin processes. However. Hammon et al. describes the use of extrudates shaped to monoliths as catalysts as being particularly disadvantageous due to rapid coking and correspondingly short service lives.

Li et al. in Catal. Lett. 2009, 129, pages 408-415 relates to a foamed ZSM-5 monolith and to the use thereof in a methanol-to-olefin process.

U.S. Pat. No. 4,049,573 relates to a catalytic process for conversion of lower alcohols and ethers thereof, and especially methanol and dimethyl ether, selectively to a hydrocarbon mixture with a high proportion of $C_2$-$C_3$ olefins and monocyclic aromatics and especially para-xylene.

Goryainova et al. in Petroleum Chemistry 2011, vol. 51, no. 3, p. 169-173 describes the catalytic conversion of dimethyl ether to lower olefins using magnesium-containing zeolites.

Even though some advances have been achieved in the prior art with regard to the selectivities and/or activities of the catalysts by alterations to their composition and/or their configuration, especially also in methanol-to-olefin processes, there is still a considerable need for new catalysts and processes which, as well as new and/or improved selectivities, also have better resistance to any deactivation in such processes. This is especially true of those improvements which can lead to lower coking of the catalyst, in order thus to be able to enable a higher efficiency of existing and new processes.

DETAILED DESCRIPTION

It was thus an object of the present invention to provide an improved catalyst, especially for the conversion of oxygenates to olefins, which enables a longer service life of the catalyst with comparable space velocity and conversion of oxygenates. In this context, it was a particular object of the present invention to bring about improvements with regard to the coking of the catalyst which, for example in methanol-to-olefin processes, decides the service lives of a catalyst before regeneration of the catalyst is required, in order to achieve the desired selectivity and/or an adequate space-time yield.

It has been found that, surprisingly, through the combined use of a gas stream comprising one or more ethers with a catalyst comprising a support substrate and a layer applied to the substrate, the catalytically active layer comprising one or more zeolites of the MFI. MEL and/or MWWW structure type, it is possible to provide a process for preparing olefins which enables considerably longer service lives of the catalyst. More particularly, it has been found that, unexpectedly, in a process for preparing olefins, an unexpected improvement in the resistance of the catalyst with respect to deactivation can be achieved during the use thereof in the case of use of such a coated support substrate as a catalyst when the reactant stream comprises one or more ethers.

Thus, the present invention relates to processes for converting ethers to olefins, comprising
(1) providing a gas stream comprising one or more ethers;
(2) contacting the gas stream provided in (1) with a catalyst,
the catalyst comprising
a support substrate and
a layer applied to the substrate,
the layer comprising one or more zeolites of the MFI, MEL and/or MWW structure type.

With regard to the support substrate used in the process according to the invention, there is in principle no restriction whatsoever with regard to the form thereof. It is thus possible in principle to select any conceivably possible form for the support substrate, provided that it is suitable for being at least partially coated with a layer of the one or more zeolites of the MFI. MEL and/or MWW structure type. According to the present invention, however, it is preferred that the form of the support substrate is selected from the group consisting of granules, pellets, meshes, rings, spheres, cylinders, hollow cylinders, monoliths and mixtures and/or combinations of two or more thereof. With respect to the preferred mixtures, these relate preferably to those forms of the support substrate which are commonly used for production of beds, this relating especially to the preferred forms of the support substrate selected from the group of the granules, pellets, meshes, rings, spheres, cylinders and hollow cylinders. On the other hand, with respect to the combinations of forms of the support substrate according to the present invention, preference is given to those combinations of beds and monoliths where the beds preferably comprise support substrates selected from the group consisting of granules, pellets, meshes, rings, spheres, cylinders, hollow cylinders and mixtures of two or more thereof. More particularly, such combinations of beds and monoliths relate to preferred forms of the catalyst in which a sequence of one or more monoliths and one or more beds is present, in which the bed(s) and monolith(s) form individual zones of the catalyst. Alternatively, however, preference is also given to embodiments of the inventive catalyst which comprise combinations of monoliths as the form of the support substrate, especially combinations of monoliths according to the particular or preferred embodiments as described in the present application. In particularly preferred embodiments of the present invention, the support substrate consists of one or more monoliths, and, in the case of use of a plurality of monoliths, a sequence and/or a succession of individual monoliths or plural monoliths arranged alongside one another at least in pairs is present in the catalyst.

Thus, according to the present invention, preference is given to embodiments of the process for converting ethers to olefins in which the form of the support substrate is selected from the group consisting of granules, pellets, meshes, rings, spheres, cylinders, hollow cylinders, monoliths and mixtures and/or combinations of two or more thereof, the support substrate preferably being one or more monoliths.

With regard to the one or more monoliths which are preferably present as the support substrate in the catalyst of the process according to the invention, there is again in principle no restriction with respect to the form that the one or more monoliths may take. According to the present invention, preference is given to monoliths selected from the group consisting of honeycombs, braids, foams and combinations of two or more thereof, and the one or more monoliths further preferably comprise one or more honeycombs and/or braids. More preferably, according to the present invention, the one or more monoliths which are preferably used as the support substrate are in honeycomb form.

Thus, according to the present invention, preference is given to embodiments of the process for converting ethers to olefins in which the one or more monoliths as the preferred support substrate are selected from the group consisting of honeycombs, braids, foams and combinations of two or more thereof, the one or more monoliths preferably being in honeycomb form.

In the preferred embodiments of the process in which the catalyst comprises one or more monoliths in honeycomb form, there are no particular restrictions whatsoever with regard to the honeycomb form, provided that it is suitable for being at least partially coated with the one or more zeolites of the MFI. MEL and/or MWW structure type. In particularly preferred embodiments, the honeycomb consists of a multitude of channels which run parallel to one another and which are divided from one another by the walls of the monolith, and the shape of the channels and/or preferably the thickness of the walls of the monolith which divide the channels from one another, up to a certain tolerance, are the same both in terms of the shape of the channels and with regard to the wall thickness, the latter typically resulting from the material used for production of the monolith or from the mode of production of the honeycomb or the honeycomb form. For example, preference is given to channels which have an angular shape, preferably the shape of a regular polyhedron having three or more vertices, preferably having three, four or six vertices and more preferably having four vertices. With regard to the dimensions of the channels in the preferred embodiments of the monoliths in honeycomb form, there is no restriction in principle, provided that the selected dimensions allow at least partial coating of the monolith in honeycomb form as the support substrate in the inventive catalyst with the one or more zeolites of the MR. MEL and/or MWW structure type. Thus, according to the present invention, it is possible to use, for example, monoliths in honeycomb form having 62 to 186 channels per square centimeter (400 to 1200 cpsi=cello per square inch), preference being given to monoliths in honeycomb form having 78 to 171 channels per square centimeter (500 to 1100 cpsi), further preference to those having 93 to 163 (600 to 1050 cpsi), further preference to those having 109 to 155 (700 to 1000 cpsi), further preference to those having 124 to 147 (800 to 950 cpsi) and further preference to those having 132 to 144 (850 to 930 cpsi). In particularly preferred embodiments of the present invention, according to which the support substrate comprises one or more monoliths in honeycomb form, those having 136 to 141 channels per square centimeter (880 to 910 cpsi) are used.

In alternative embodiments of the present invention which use one or more monoliths as the support substrate in the catalyst, no substrate foams are present therein. Thus, preference is likewise given to embodiments of the catalyst used in the process in which the support substrate does not comprise any foams and more particularly does not comprise any foams as a monolith.

With regard to the substance of which the support substrate consists, and especially the beds and/or monoliths present therein, according to the present invention, there are no restrictions whatsoever in this regard, provided that it is suitable for being at least partially coated with the one or more zeolites of the MFI, MEL and/or MWW structure type. Thus, it is possible in principle to use any suitable material and/or any material composite as the substance for the support substrate, preference being given to using those materials which have high thermal stability and/or are inert to a high degree with regard to the chemical reactivity thereof. Thus, preference is given to using ceramic and/or metallic substances and composite materials of ceramic and/or metallic substances as the support substrate in the inventive catalyst, preference being given to using ceramic substances as the support substrate. With regard to the preferred ceramic substances, preference is given to using one or more of these substances selected from the group consisting of alumina, silica, silicates, aluminosilicates, silicon carbide, cordierite, mullite, zirconium, spinels, magnesia, titania and mixtures of two or more thereof. In a particularly preferred embodiment of the present invention, the ceramic substances preferably used for the support substrate are selected from the group consisting of α-alumina, silicon carbide, cordierite and mixtures of two or more thereof. In particularly preferred embodiments, the support substrate comprises cordierite, the support substrate further preferably being a cordierite substrate.

Thus, according to the present invention, preference is given to embodiments of the process for converting ethers to olefins in which the support substrate comprises ceramic and/or metallic substances, preferably ceramic substances, further preferably one or more substances selected from the group consisting of alumina, silica, silicates, aluminosilicates, silicon carbide, cordierite, mullite, zirconium, spinels, magnesia, titanic and mixtures of two or more thereof, preferably from the group consisting of alpha-alumina, silicon carbide, cordierite and mixtures of two or more thereof, the support substrate more preferably being a cordierite substrate.

With regard to the one or more zeolites present in the catalyst, according to the present invention, there are no restrictions whatsoever either with respect to the type or with respect to the number of zeolites which can be used herein, provided that they are zeolites of one or more of the MFI, MEL and MWW structure types. If one or more of the zeolites present in the catalyst are of the MWW structure type, there is again no restriction whatsoever with respect to the type and/or number of MWW zeolites which can be used according to the present invention. Thus, these may be selected, for example, from the group of zeolites of the MWW structure type consisting of MCM-22, MCM-36, [Ga—Si—O]-MWW, [Ti—Si—C]-MWW, ERB-1, ITQ-1, PSH-3, SSZ-25 and mixtures of two or more thereof, preference being given to the use of zeolites of the MWW structure type which are suitable for the conversion of ethers to olefins, especially MCM-22 and/or MCM-36.

The same applies correspondingly to the zeolites of the MEL structure type which can be used according to the present invention in the catalyst, these being selected, for example, from the group consisting of ZSM-11, [Si—B—O]-MEL, boron-D (MFI/MEL mixed crystal), boralite D, SSZ-46, silicalite 2, TS-2 and mixtures of two or more thereof. Here too, preference is given to using those zeolites of the MEL structure type which are suitable for the conversion of ethers to olefins, especially [Si—B—O]-MEL.

According to the present invention, however, especially zeolites of the MFI structure type are used in the catalyst of the process according to the invention for converting ethers to olefins. With regard to these preferred embodiments of the present invention, there is likewise no restriction whatsoever with respect to the type and/or number of the zeolites of this structure type which are used, the one or more zeolites of the MFI structure type which are used in the inventive catalyst preferably being selected from the group consisting of ZSM-5, ZBM-10, [As—Si—O]-MFI, AMS-1B, AZ-1, boron-C, boralite C, encilite, FZ-1, LZ-105, monoclinic H-ZSM-5, mutinaite, NU-4, NU-5, silicalite, TS-1, TSZ, TSZ-III, TZ-01, USC-4, USI-108, ZBH, ZKQ-1B, ZMQ-TB and mixtures of two or more thereof. Further preferably, according to the present invention, the catalyst comprises ZSM-5 and/or ZBM-10 as the zeolite of the MFI structure type, particular preference being given to using ZSM-5 as the zeolite. With regard to the zeolitic material ZBM-10 and the preparation thereof, reference is made, for example, to EP 0 007 081 A1 and to EP 0 034 727 A2, the content of which, particularly with regard to the preparation and characterization of the material, is hereby incorporated into the present invention.

Thus, according to the present invention, preference is given to embodiments of the process for converting ethers to olefins in which the one or more zeolites are of the MFI structure type, and are preferably selected from the group consisting of ZSM-5, ZBM-10, [As—Si—O]-MFI, [Fe—Si—O]-MFI, [Ga—Si—O]-MR, AMS-1B, AZ-1, boron-C, boralite C, encilite, FZ-1. LZ-105, monoclinic H-ZSM-5, mutinaite, NU-4, NU-5, silicalite, TS-1, TSZ, TSZ-III, TZ-01, USC-4, USI-108, ZBH, ZKQ-1B, ZMQ-TB and mixtures of two or more thereof, further preferably from the group consisting of ZSM-5. ZBM-10 and mixtures thereof, the zeolite of the MFI structure type preferably being ZSM-5.

In a preferred embodiment of the present invention, the catalyst does not comprise any significant amounts of one or more nonzeolitic materials and especially does not comprise any significant amounts of one or more aluminosilicophosphates (SAPOs). In the context of the present invention, the catalyst is essentially free of or does not comprise any significant amounts of a specific material in cases in which this specific material is present in the catalyst in an amount of 0.1% by weight or less based on 100% by weight of the total amount of the one or more zeolites of the MFI, MEL and/or MWW structure type, preferably in an amount of 0.05% by weight or less, further preferably of 0.001% by weight or less, further preferably of 0.0005% by weight or less and further preferably in an amount of 0.0001% by weight or less. A specific material in the context of the present invention particularly denotes a particular element or a particular combination of elements, a particular substance or a particular substance mixture, and also combinations and/or mixtures of two or more thereof.

The aluminosilicophosphates (SAPOs) in the context of the present invention include especially the SAPO materials SAPO-11, SAPO-47, SAPO-40, SAPO-43, SAPO-5, SAPO-31, SAPO-34, SAPO-37, SAPO-35, SAPO-42, SAPO-56, SAPO-18, SAPO-41, SAPO-39 and CFSAPO-1A.

With regard to the form in which the one or more zeolites of the MFI. MEL and/or MWW structure type is used in the catalyst of the process according to the invention for converting ethers to olefins, there is no restriction whatsoever in principle, especially with respect to the further elements or compounds which may be present therein. Thus, there are generally no restrictions whatsoever with regard to the ions and compounds which may be present in the micropores of the one or more zeolites, especially with respect to the counterions to the possibly negatively charged zeolite skeleton which are present in the micropores. Accordingly, the one or more zeolites may be in a form in which the possibly negative charge of the zeolite skeleton is compensated for by one or more different cationic elements and/or compounds, this preferably being accomplished at least partly by means of one or more cationic elements and/or compounds selected from the group consisting of $H^+$, $NH_4^+$, $Li^+$, $Na^+$, $K^+$ and combinations of two or more thereof, further preferably from the group consisting of $H^+$, $Na^+$, $K^+$ and combinations of two or more thereof. In particularly preferred embodiments of the present invention, the one or more zeolites of the MFI, MEL and/or MWW structure type optionally comprise $H^4$ and/or $Na^+$, and preferably $H^+$ as the counterion to the negatively charged zeolite skeleton, which means that the one or more zeolites of the MFI, MEL and/or MWW structure type are more preferably used in the respective H form thereof in the catalyst of the process according to the invention.

With regard to the amount in which the one or more zeolites of the MFI, MEL and/or MWW structure type has been applied to the support substrate in the catalyst according to the present invention, there is in principle no restriction whatsoever, provided that a layer comprising the one or more zeolites can be formed at least partially on the support substrate. Thus, the inventive catalysts comprise, for example, the one or more zeolites of the MFI, MEL and/or MWW structure type in a total loading of 0.005-1 $g/cm^3$. The volume relates here to the volume of the coated support substrate, and this in the case of bodies and forms comprising hollow bodies and/or recesses also comprises those cavities and recesses. In an alternative definition according to the present invention, the volume in the case of the loading of the support substrate, in embodiments comprising beds, is based on the respective volume of the bed including the intermediate spaces and cavities present therein. In preferred embodiments of the present invention, the catalyst comprises the one or more zeolites of the MFI, MEL and/or MWW structure type in a total loading of 0.01-0.5 $g/cm^3$ based on the volume of the coated support substrate and especially on the volume thereof according to the aforementioned particular and preferred definitions, further preferably in a total loading of 0.02-0.2 $g/cm^3$, further preferably of 0.04-0.1 $g/cm^3$, further preferably of 0.055-0.08 $g/cm^3$ and further preferably of 0.065-0.075 $g/cm^3$. In particularly preferred embodiments of the present invention, the catalyst comprises the one or more zeolites of the MFI, MEL and/or MWW structure type in a total loading of 0.07-0.072 $g/cm^3$ based on the volume of the coated support substrate according to the particular and preferred definitions of the present invention.

Thus, according to the present invention, preference is given to embodiments of the process for converting ethers to olefins in which the catalyst comprises the one or more zeolites of the MR, MEL and/or MWW structure type in a total loading of 0.005 to 1 $g/cm^3$ based on the volume of the coated support substrate, preferably in a total loading of 0.01 to 0.5 $g/cm^3$, further preferably of 0.02 to 0.2 $g/cm^3$, further preferably of 0.04 to 0.1 $g/cm^3$, further preferably of 0.055 to 0.08 $g/cm^3$, further preferably of 0.065 to 0.075 $g/cm^3$, and further preferably in a total loading of 0.07 to 0.072 $g/cm^3$.

The same applies correspondingly to the one or more ethers present in the gas stream according to (1), and so there is no restriction here whatsoever in principle in the process according to the invention, provided that the one or more ethers present in the gas stream according to (1) can be converted by one of the catalysts according to the present invention and especially according to the particular and preferred embodiments thereof to at least one olefin when contacted according to (2). According to the present invention, however, it is preferable that the one or more ethers present in the gas stream according to (1) is selected from the group consisting of di($C_1$-$C_3$)alkyl ethers and mixtures of two or more thereof. Further preferably, the one or more ethers are selected from the group consisting of dimethyl ether, diethyl ether, ethyl methyl ether, diisopropyl ether, di-n-propyl ether and mixtures of two or more thereof, the one or more ethers further preferably being selected from the group consisting of dimethyl ether, diethyl ether, ethyl methyl ether and mixtures of two or more thereof. In particularly preferred embodiments of the process according to the invention for converting ethers to olefins, the gas stream according to (1) comprises dimethyl ether as the one or more ethers, and dimethyl ether is more preferably the ether present in the gas stream according to (1).

Thus, according to the present invention, preference is given to embodiments of the process for converting ethers to olefins in which the gas stream according to (1) comprises one or more di($C_1$-$C_3$)alkyl ethers, preferably one or more ether compounds selected from the group consisting of dimethyl ether, diethyl ether, ethyl methyl ether, di-n-propyl ether, diisopropyl ether, and mixtures of two or more thereof, further preferably from the group consisting of dimethyl ether, diethyl ether, ethyl methyl ether and mixtures of two or more thereof, the gas stream according to (1) further preferably comprising dimethyl ether.

On the other hand, with regard to the content of ethers in the gas stream according to (1) in the process according to the invention for converting ethers to olefins, there is no restriction whatsoever according to the present invention here either, provided that, when the gas stream is contacted in (2) with a catalyst according to the present invention, at least one ether can be converted to at least one olefin. In preferred embodiments, the content of ethers in the gas stream according to (1) is in the range from 30 to 100% by volume based on the total volume, the content especially being based on a gas stream at a temperature in the range from 200 to 700° C. and at a pressure of 101.3 kPa, preferably at a temperature in the range from 250 to 650° C., further preferably from of 300 to 600° C., further preferably from 350 to 560° C., further preferably from 400 to 540° C., further preferably from 430 to 520° C., and further preferably in the range from 450 to 500° C. and at a pressure of 101.3 kPa. According to the present invention, it is further preferred that the content of ethers in the gas stream according to (1) is in the range from 30 to 99% by volume, further preferably from 30 to 95% by volume, further preferably from 30 to 90% by volume, further preferably from 30 to 80% by volume, further preferably from 30 to 70% by volume, further preferably from 30 to 60% by volume and further preferably from 30 to 50% by volume. In particularly preferred embodiments of the process according to the invention for converting ethers to olefins, the content of ethers in the gas stream according to (1) is in the range from 30 to 45% by volume.

Thus, according to the present invention, preference is given to embodiments of the process for converting ethers to olefins in which the content of ethers in the gas stream according to (1) is in the range from 30 to 100% by volume based on the total volume, preferably from 30 to 99% by volume, further preferably from 30 to 95% by volume, further preferably from 30 to 90% by volume, further preferably from 30 to 80% by volume, further preferably from 30 to 70% by volume, further preferably from 30 to 60% by volume, further preferably from 30 to 50% by volume, and further preferably from 30 to 45% by volume.

According to the present invention, there is no restriction whatsoever in principle with respect to the composition of the gas stream in (1), provided that at least one of the ethers present in the gas stream can be converted to at least one olefin in the process according to the invention. Thus, there is also no restriction whatsoever with respect to the origin of the gas stream provided in (1), provided that the aforementioned condition of the conversion of at least one ether to at least one olefin has been correspondingly fulfilled. Accordingly, the gas stream may in principle be composed of one or more ethers and one or more additional compounds to give a gas stream. In particularly preferred embodiments of the process according to the invention for chemically converting ethers to olefins, the gas stream provided in (1) originates from at least one preliminary reaction, preferably from the chemical conversion of one or more alcohols to one or more ethers, the one or more alcohols preferably being selected from the group of the aliphatic aliphatic alcohols. In further preferred embodiments, at least a portion of the gas stream provided in (1) originates from the chemical conversion of one or more aliphatic ($C_1$-$C_6$) alcohols and mixtures of two or more thereof, further preferably from the conversion of one or more aliphatic ($C_1$-$C_4$) alcohols and mixtures of two or more thereof, further preferably from the chemical conversion of one or more aliphatic alcohols selected from the group consisting of methanol, ethanol, n-propanol, isopropanol, butanol and mixtures of two or more thereof, further preferably from the group consisting of methanol, ethanol, n-propanol and mixtures of two or more thereof, the gas stream provided in (1) more preferably originating from a preliminary reaction of methanol and/or ethanol and methanol further preferably being at least partly converted to one or more di($C_1$-$C_2$)alkyl ethers, preferably to one or more di($C_1$-$C_2$)alkyl ethers selected from the group consisting of dimethyl ether, diethyl ether, ethyl methyl ether and mixtures of two or more thereof. For instance, the gas stream provided in (1), in a particularly preferred embodiment, originates from a preliminary reaction of conversion of methanol to dimethyl ether.

In the particularly preferred embodiments of the process according to the invention in which the gas stream provided in (1) originates from a preliminary reaction of one or more alcohols, there is no particular restriction whatsoever in principle with respect to the reaction and hence the reaction product of the conversion of one or more alcohols, provided that this leads to a gas stream comprising one or more ethers which, when contacted in (2) with a catalyst according to the present invention, enables the conversion of at least one of the ethers to at least one olefin. In these particular embodiments, it is further preferable that the preliminary reaction leads to conversion of at least one alcohol to at least one ether and especially to at least one dialkyl ether, the preliminary reaction more preferably being a dehydration in which water is obtained as a coproduct to one or more dialkyl ethers. In the particular and preferred embodiments of the present invention in which the gas stream provided in (1) originates from a preliminary reaction, it is particularly preferred in the process according to the invention that such a gas stream originating from a preliminary reaction is supplied directly and without workup to the process according to the invention in step (1).

Thus, according to the present invention, preference is given to embodiments of the process for converting ethers to olefins in which the gas stream according to (1) is obtainable from a preliminary stage, preferably from a preliminary stage of the dehydration of one or more aliphatic alcohols, preferably of one or more ($C_1$-$C_6$) alcohols, further preferably of one or more ($C_1$-$C_4$) alcohols, further preferably of one or more aliphatic alcohols selected from the group consisting of methanol, ethanol, n-propanol, isopropanol, butanol and mixtures of two or more thereof, further preferably from a preliminary stage of the dehydration of methanol and/or ethanol, preferably of methanol.

With regard to the dehydration which is preferably performed in the preliminary stage for providing the gas stream in (1), according to particularly preferred embodiments of the process according to the invention, there are again no restrictions whatsoever with respect to the manner in which this is performed, provided that at least one alcohol and preferably at least one aliphatic alcohol is chemically converted to at least one ether. In preferred embodiments, the dehydration is at least partly a catalytic dehydration, and there is in principle no restriction whatsoever with respect to the catalyst used for this purpose, provided that it is capable under the selected conditions of the preliminary reaction of catalytically converting at least one alcohol and preferably at least one aliphatic alcohol to at least one ether, preferably with simultaneous formation of water. In particularly preferred embodiments of the process according to the invention, a heterogeneous catalyst is used for the preferred dehydration as the preliminary reaction, the catalyst preferably being in solid form and preferably having acidic sites, at least some of these preferably being in the form of Lewis-acidic sites. Thus, in these particularly preferred embodiments of the process according to the invention, for example, alumina is used as the heterogeneous catalyst for the preliminary reaction, and, in a particularly preferred embodiment, gamma-alumina is used as the heterogeneous catalyst for the dehydration.

With respect to the reaction conditions which are selected for the dehydration in the preferred embodiments of the process according to the invention, there are no restrictions in principle in this respect either, provided that at least one alcohol and preferably at least one aliphatic alcohol can be chemically converted to at least one ether. With regard to the temperature selected for the dehydration, it is thus possible to set any temperature suitable for this purpose, and, in the case of the dehydration according to the particular or preferred embodiments in which a heterogeneous catalyst is used, the temperature for the preliminary reaction is preferably in the range from 100 to 600° C., further preferably from 150 to 500° C., further preferably from 200 to 400° C., further preferably from 230 to 350° C., further preferably from 250 to 300° C., and further preferably from 270 to 280° C.

With regard to the other components in the gas stream according to (1) in the process according to the invention, there is in principle no restriction whatsoever, provided that the gas stream is suitable overall for conversion of at least one of the ethers to at least one olefin in step (2) when contacted with a catalyst according to the present invention. In addition, for example, as well as the one or more ethers in the gas stream according to (1), one or more inert gases may also be present therein, for example one or more noble gases, nitrogen, water and mixtures of two or more thereof. In particular embodiments of the present invention, the gas stream according to (1) of the process according to the invention, as well as the one or more ethers, comprises water, this being especially true of the particular and preferred embodiments of the present invention in which the gas stream according to (1) is obtained from a preliminary stage of dehydration.

With respect to those preferred embodiments in which, as well as the one or more ethers, water is present in the gas stream according to (1), there is no restriction in principle with respect to the water content which may be present therein, provided that the conversion of at least one ether in the gas stream to at least one olefin in step (2) of the contacting of the gas stream can be effected with a catalyst according to the present invention. In those preferred embodiments, however, it is preferable that the water content in the gas stream is in the range from 5 to 60% by volume based on the total volume, the water content more preferably being in the range from 10 to 55% by volume, further preferably from 20 to 50% by volume and further preferably from 30 to 45% by volume.

Thus, according to the present invention, preference is given to embodiments of the process for converting ethers to olefins in which water is present in the gas stream according to (1), preferably in the range from 5 to 60% by volume based on the total volume, preferably from 10 to 55% by volume, further preferably from 20 to 50% by volume, and further preferably from 30 to 45% by volume.

With respect to the manner of contacting the gas stream with a catalyst according to the present invention in step (2) of the process according to the invention for converting ethers to olefins, there is in principle no restriction whatsoever, provided that the conversion of at least one ether to at least one olefin can be implemented. This applies, for example, to the temperature at which the contacting (2) takes place. Thus, for example, the contacting in step (2) of the process according to the invention can take place at a temperature in the range from 200 to 700° C., preference being given to selecting temperatures in the range from 250 to 650° C., further preferably from 300 to 600° C., further preferably from 350 to 560° C., further preferably from 400 to 540° C. and further preferably from 430 to 520° C. In particularly preferred embodiments of the present invention, the contacting according to (2) of the process according to the invention is performed at a temperature in the range from 450 to 500° C.

Thus, according to the present invention, preference is given to embodiments of the process for converting ethers to olefins in which the contacting according to (2) is effected at a temperature in the range from 200 to 700° C., preferably from 250 to 650° C., further preferably from 300 to 600° C., further preferably from 350 to 560° C., further preferably from 400 to 540° C., further preferably from 430 to 520° C., and further preferably from 450 to 500° C.

The same applies correspondingly to the pressure at which the gas stream is contacted in step (2) of the process according to the invention with the catalyst according to the present invention. Thus, the contacting can in principle take place at any desired pressure, provided that this allows the conversion of at least one ether to at least one olefin by virtue of the contacting of the gas stream with the catalyst. Thus, the pressure, for example in the contacting in step (2), may be in the range from 0.1 to 10 bar, the pressure according to the present application indicating the absolute pressure, such that a pressure of 1 bar in the contacting accordingly corresponds to the standard pressure of 1.03 kPa. According to the present invention, the contacting in step (2) takes place preferably at a pressure from 0.3 to 7 bar, further preferably from 0.5 to 5 bar, further preferably from 0.7 to 3 bar, further preferably from 0.8 to 2.5 bar and further preferably from 0.9 to 2.2 bar. In particularly preferred embodiments of the process according to the invention for converting ethers to olefins, the contacting in step (2) takes place at a pressure of 1 to 2 bar.

Thus, according to the present invention, preference is given to embodiments of the process for converting ethers to olefins in which the contacting according to (2) is effected at a pressure in the range from 0.1 to 10 bar, preferably from 0.3 to 7 bar, further preferably from 0.5 to 5 bar, further preferably from 0.7 to 3 bar, further preferably from 0.8 to 2.5 bar, further preferably from 0.9 to 2.2 bar, and further preferably from 1 to 2 bar.

In addition, there are no particular restrictions with respect to the manner of performance of the process according to the invention for converting ethers to olefins, and so it is possible to use either a continuous or a noncontinuous process, the noncontinuous process being performable, for example, in the form of a batch process. According to the present invention, however, it is preferable to conduct the process according to the invention for the conversion of ethers as a continuous process. Thus, according to the present invention, preference is given to embodiments of the process for converting ethers to olefins in which the process is a continuous process.

With respect to these preferred embodiments of a continuous process, there are no restrictions whatsoever with respect to the space velocity selected, provided that the conversion of an ether to an olefin can be effected. Thus, it is possible to select, for example, space velocities in the contacting in step (2) which are in the range from 0.5 to 50 $h^{-1}$, preference being given to selecting space velocities (WHSV=weight hourly space velocity is calculated as the ratio of oxygenate reactant stream in kg/h to the amount of zeolite in the reactor in kg) from 1 to 30 $h^{-1}$, further preferably from 3 to 25 $h^{-1}$, further preferably from 5 to 20 $h^{-1}$, further preferably from 7 to 15 $h^{-1}$ and further preferably from 8 to 12 $h^{-1}$. In particularly preferred embodiments of the process according to the invention for converting ethers, space velocities for the contacting of the gas stream in step (2) in the range from 9 to 11 $h^{-1}$ are selected.

Thus, according to the present invention, preference is given to embodiments of the process for converting ethers to olefins in which the space velocity in the course of contacting according to (2) is in the range from 0.5 to 50 $h^{-1}$, preferably from 1 to 30 $h^{-1}$, further preferably from 3 to 25 $h^{-1}$, further preferably from 5 to 20 $h^{-1}$, further preferably from 7 to 15 $h^{-1}$, further preferably from 8 to 12 $h^{-1}$, and further preferably from 9 to 11 $h^{-1}$.

As described above and shown in the examples of the present application, it is possible to achieve particularly long service lives with the inventive catalyst in a process for converting ethers as described in the present application, especially with respect to the particular and preferred embodiments of the process according to the invention. It has thus been found that, surprisingly, the use of a catalyst according to the present invention can considerably increase the service life of the catalyst before the process has to be interrupted for regeneration of the catalyst, at least with respect to the use of this catalyst batch compared to the use of catalysts according to the prior art. It is thus particularly preferable according to the present invention to select long service lives for the performance of the process for converting ethers to olefins at one of the particular or preferred space velocities, as described in the present application.

Thus, preference is given to service lives in the range from 15 to 200 h, further preferably in the range from 20 to 150 h, further preferably from 25 to 100 h, further preferably from 30 to 80 h, further preferably from 35 to 70 h, further preferably from 40 to 65 h, further preferably from 45 to 60 h and further preferably from 50 to 55 h. More particularly, based on the particular and preferred space velocities at which the process according to the invention is performed, preference is thus given, for example, to service lives of 15 to 200 h at a space velocity in the range from 0.5 to 50 h$^{-1}$. Preference is further given to a service life from 20 to 150 h at a space velocity of 1 to 30 h$^{-1}$, further preference to a service life from 25 to 100 h at a space velocity of 1 to 30 h$^{-1}$, further preference to a service life from 30 to 80 h at a space velocity of 3 to 25 h$^{-1}$, further preference to a service life from 35 to 70 h at a space velocity in the range from 5 to 20 h$^{-1}$, further preference to a service life from 40 to 65 h at a space velocity in the range from 7 to 15 h$^{-1}$ and further preferably from 45 to 60 h at a space velocity of 8 to 12 h$^{-1}$. In a particularly preferred embodiment of the process according to the invention, a service life of the catalyst, during which the continuous process is performed without interruption, in the range from 50 to 55 h at a space velocity of 9 to 11 h$^{-1}$ is selected. According to the present invention, the particular and preferred embodiments with respect to the service life selected and especially the service lives selected in combination with particular space velocities preferably relate to a minimum conversion of the one or more ethers present in the gas stream according to (1) of the process according to the invention, sustained conversion below this value leading to subsequent performance of the regeneration of the catalyst. According to the present invention, there is no particular restriction with respect to the minimum conversion selected, this preferably allowing full conversion of the one or more ethers present in the gas stream according to (1) of the process according to the invention during the service life of the catalyst. Thus, in preferred embodiments of the present invention, a minimum conversion of 60% of the one or more ethers present in the gas stream according to (1) of the process according to the invention is selected, sustained conversion below this value leading to performance of the regeneration of the catalyst, preferably a minimum conversion of 70% or more, further preferably of 80% or more, further preferably of 85% or more, further preferably of 90% or more, further preferably of 95% or more, further preferably of 97% or more, further preferably of 98% or more, and further preferably of 99% or more of the one or more ethers present in the gas stream according to (1) of the process according to the invention.

Thus, according to the present invention, further preference is given to embodiments of the process for converting ethers to olefins in which the service life of the coated support substrate as a catalyst, during which the continuous process is performed without interruption, is in the range from 15 to 200 h, preferably from 20 to 150 h, further preferably from 25 to 100 h, further preferably from 30 to 80 h, further preferably from 35 to 70 h, further preferably from 40 to 65 h, further preferably from 45 to 60 h, and still further preferably from 50 to 55 h.

According to the present invention, the catalyst can be regenerated in principle in order to be reused in the process according to the invention. With regard to the regeneration of the catalyst, there are no restrictions whatsoever, provided that this leads to the regeneration to an at least partial re-establishment of the original activity thereof in the conversion of oxygenates to olefins. In a particularly preferred embodiment of the process according to the invention, the catalyst is regenerated by thermal treatment and especially by calcination and reused in the process.

Thus, according to the present invention, preference is given to embodiments of the process for converting ethers to olefins in which the process comprises the further steps of
(3) calcining the catalyst for regeneration;
(4) providing a gas stream comprising one or more ethers;
(5) contacting the gas stream provided in (4) with the regenerated catalyst.

With regard to the calcination of the catalyst in (3), there are no restrictions whatsoever in principle, either with regard to the duration or with regard to the temperature for calcination, provided that it contributes to an at least partial re-establishment of the original catalytic activity in the conversion of oxygenates to olefins. For example, the calcination can be performed at a temperature in the range from 200 to 1100° C., preference being given to temperatures in the range from 250 to 900° C., and further preferably in the range from 300 to 800° C., further preferably in the range from 350 to 700° C., further preferably in the range from 400 to 600° C., further preferably in the range from 450 to 550° C., and further preferably in the range from 475 to 525° C. With regard to the duration of the calcination, this can be performed, for example, for a period of 0.25 to 30 h, the duration calcination preferably being in the region of 0.5 to 20 h, further preferably from 1 to 15 h, further preferably from 1.5 to 12 h, further preferably from 2 to 10 h, further preferably from 3 to 8 h, further preferably from 3.5 to 7 h, further preferably from 4 to 6 h, and further preferably from 4.5 to 5.5 h.

The calcination in (3) for regeneration of the catalyst can in principle be performed in any suitable atmosphere, provided that at least partial re-establishment of the original activity can be achieved. Thus, the calcination can be performed, for example, in oxygen or in an oxygen-comprising atmosphere such as air or in a mixture of oxygen and an inert gas such as nitrogen and/or one or more noble gases. In preferred embodiments, the calcination in (3) is performed in air or in a mixture of oxygen and an inert gas, the calcination in (3) more preferably being effected in air atmosphere.

In principle, the catalyst can be regenerated by the preferred embodiments by which it is regenerated (3) at any suitable time in the process, provided that this leads to at least partial re-establishment of the original activity when the catalyst used had yet to be used in the conversion of oxygenates to olefins and more particularly when it was still fresh or freshly regenerated. Thus, the calcination in (3) for regeneration of the catalyst can be performed, for example, when the methanol conversion in the process for conversion of oxygenates to olefins falls below 70%, the regeneration preferably being performed when the methanol conversion in the reaction falls to 70%, and further preferably to 75%, further preferably to 80%, further preferably to 85%, further preferably to 90%, further preferably to 95%, and further preferably to 97%.

With regard to the step, which follows the calcination in (3), of providing a gas stream comprising one or more ethers in (4) and of contacting the gas stream with the regenerated catalyst in (5), these steps are in principle performed analogously to steps (1) and (2) of the process according to the invention, and more particularly according to the particular and preferred embodiments of steps (1) and (2) as defined in the present application. Thus, all particular and preferred embodiments for step (1) apply in the same way to step (4) and, independently of this, all particular and preferred embodiments for step (2) also apply in the same way to step (5).

With regard to the preferred embodiments of the process according to the invention in which the catalyst is subjected to a calcination for regeneration of the catalyst, it has been found in an entirely surprising manner that the regeneration led to a further improvement in the service life of the catalyst, even though the opposite effect would be expected in the case of an already used catalyst. Given that, the additional effect that it was possible to distinctly enhance the selectivities of the catalyst for $C_3$ and $C_4$ olefins through the calcination was all the more surprising. Thus, the preferred calcination of the catalyst in (3) serves not just for the regeneration thereof but also leads unexpectedly to an enhancement both of the service life and of the selectivity of the catalyst for $C_3$ and $C_4$ olefins as products of the conversion of oxygenates, especially in the particular and preferred embodiments of the process according to the invention.

Finally, steps (3) to (5) of the preferred embodiments of the process according to the invention can be repeated as desired, and so they can be repeated, for example, once to 1000 times. According to the present invention, it is preferable, however, that steps (3) to (5) are repeated 5 to 800 times, further preferably 10 to 700 times, more preferably 15 to 600 times, further preferably 20 to 500 times, further preferably 25 to 400 times, and further preferably 30 to 300 times.

The catalyst used in the process according to the present invention can in principle be prepared in any suitable manner, provided that it comprises one or more zeolites of the MR. MEL and/or MWW structure type which are present in a layer applied to a support substrate according to the present invention and especially according to one of the particular and preferred embodiments of the invention as described in the present application. According to the present invention, the catalyst for use in the process according to the invention is preferably obtainable by one of the processes described in the present application for preparation thereof, preferably by one of the particular or preferred processes for preparation thereof, and, in particularly preferred embodiments of the present invention, it is obtained by one of the processes described in the present application, preferably by one of the particular or preferred processes for preparation thereof.

Thus, according to the present invention, preference is further given to embodiments of the process for converting ethers to olefins in which the catalyst, and especially the catalyst obtainable by one of the particular or preferred embodiments of the process according to the invention, is obtainable by a process comprising
  (i) providing the support substrate and the one or more zeolites of the MFI, MEL and/or MWW structure type;
  (ii) preparing a mixture comprising the one or more zeolites of the MFI. MEL and/or MWW structure type and one or more solvents;
  (iii) homogenizing the mixture obtained in (ii);
  (iv) coating the support substrate with the homogenized mixture obtained in (iii);
  (v) optionally drying the coated support substrate obtained in (iv);
  (vi) optionally calcining the coated support substrate obtained in (iv) or (v).

With regard to the process for preparing the catalyst used in the process according to the invention, especially in the particular and preferred embodiments described in the present application, there is in principle no restriction whatsoever with respect to the properties and especially the particle sizes and morphologies of the one or more zeolites of the MFI. MEL and/or MWW structure type provided in step (i). According to the particle size of the zeolites provided in step (i), however, one or more steps are optionally performed during the process according to the invention, preferably prior to the provision of the one or more zeolites in (i) or after the preparation of the mixture in step (ii), in order to bring the one or more zeolites to a preferred particle size. In this connection, there is at first no particular restriction with regard to the particle size of the one or more zeolites, provided that this is suitable for the performance of the further steps in the process according to the invention, especially according to the particular and preferred embodiments of the present invention, and the particle size should especially be suitable for performance of the coating in step (iv), more particularly depending on the nature and form of the support substrate used according to the present invention and especially according to the particular or preferred embodiments of the support substrate as described in the present application. Thus, in particular embodiments of the process according to the invention, one or more steps are performed prior to the provision of the one or more zeolites in (i) or after the preparation of the mixture in step (ii), preferably after the preparation of the mixture in step (ii) and more preferably in step (iii) of the homogenizing of the mixture obtained in (ii), in order to bring the one or more zeolites of the MFI, MEL and/or MWW structure type to a particle size D50 in the range from 0.01 to 200 µm. In further preferred embodiments of the process according to the invention, the one or more zeolites are brought after one or more of the aforementioned steps, in one or more steps, to a particle size D50 in the range from 0.03 to 150 µm, further preferably from 0.05 to 100 µm, further preferably from 0.1 to 50 µm, further preferably from 0.3 to 30 µm and even further preferably from 0.4 to 20 µm. In yet further preferred embodiments of the process according to the invention, the one or more zeolites, after the preparation of the mixtures in step (ii) and preferably in step (iii) of the homogenizing of the mixture obtained in (ii), is brought in one or more steps to a particle size D50 in the range from 0.5 to 15 µm. With regard to the number of steps and the manner in which the one or more zeolites are brought to a particular or preferred particle size D50, according to the present invention, there are no restrictions whatsoever, and so it is possible in principle to use any suitable process for this purpose. According to the present invention, the one or more zeolites, however, are preferably subjected to one or more grinding steps prior to the provision of the one or more zeolites in (i) or after the preparation of the mixture in step (ii), preferably after the preparation of the mixture in step (ii), and the one or more zeolites are more preferably brought to one of the particular or preferred particle sizes D50 by the operation of homogenizing in step (iii), especially according to the particular and preferred embodiments of the present invention.

Thus, according to the present invention, preference is given to embodiments of the process for preparing the catalyst, and especially the catalyst according to one of the particular or preferred embodiments thereof, in which the provision of the one or more zeolites in (i) is preceded or the preparation of the mixture in step (ii) is followed, preferably the preparation of the mixture in step (ii) and more preferably in step (iii) of the homogenizing of the mixture obtained in (ii) is followed, by bringing of the one or more zeolites of the MFI, MEL and/or MWW structure type to a particle size D50 in the range from 0.01 to 200 µm, further preferably from 0.03 to 150 µm, further preferably from 0.05 to 100 µm, further preferably from 0.1 to 50 µm, further preferably from 0.3 to 30 µm, further preferably from 0.4 to 20 µm, even further preferably from 0.5 to 15 µm.

According to the present invention, in the preferred process for preparing the catalyst, a drying step according to step (v) is optionally performed. With regard to the manner in which the optional drying is achieved, there is no restriction whatsoever in principle, and so the drying can be performed at any suitable temperature and in any suitable atmosphere. Thus, the optional drying can be effected under a protective gas atmosphere or in air, the optional drying preferably being effected in air. With regard to the temperature at which the drying is effected, it is possible, for example, to select a temperature in the range from 50 to 220° C. According to the present invention, the optional drying according to step (v) is effected at a temperature in the range from 70 to 180° C., further preferably from 80 to 150° C., further preferably from 90 to 130° C. and further preferably in the range from 100 to 120° C. In particularly preferred embodiments of the process according to the invention, the drying according to step (v) is effected at a temperature in the range from 105 to 115° C. With regard to the duration of the one or more optional drying steps, especially in particular and preferred embodiments of the process according to the invention, there is no particular restriction, provided that drying suitable for the further process steps can be achieved, for example after a drying step having a duration of 0.1 to 20 hours. In particular embodiments of the process according to the invention, the optional drying is performed for a period of 0.3 to 10 h, further preferably of 0.5 to 5 h, further preferably of 0.8 to 2 h and still further preferably of 0.9 to 1.5 h.

Thus, according to the present invention, preference is given to embodiments of the process for preparing the catalyst, and especially the catalyst according to one of the particular or preferred embodiments thereof, in which the drying in (v) is effected at a temperature in the range from 50 to 220° C., preferably from 70 to 180° C., further preferably from 80 to 150° C., further preferably from 90 to 130° C., further preferably from 100 to 120° C., and further preferably from 105 to 115° C.

With regard to the optional calcining according to the present invention, the same applies in principle as with regard to the optional drying step, and so no particular restriction whatsoever exists here either, either with regard to the temperature or with regard to the atmosphere in which the calcination is performed, and finally also not with regard to the duration of a calcination according to the particular and preferred embodiments of the present invention, provided that the product of the calcination is an intermediate suitable for being processed in the further steps of the process according to the invention to give a catalyst according to the present invention. Thus, for example, with regard to the temperature of the optional calcining in step (vi), a temperature in the range from 300 to 850° C. may be selected, preference being given to selecting a temperature in the range from 400 to 750° C., further preferably from 450 to 700° C., further preferably from 500 to 650° C. and even further preferably from 530 to 600° C. In yet further preferred embodiments of the present invention, the calcination in the optional step (vi) is performed at a temperature of 540 to 560° C. With respect to the atmosphere in which the optional calcination according to one or more of the aforementioned steps of the process according to the invention is performed, this may be either an inert atmosphere or air, the optional calcination in step (vi) preferably being performed in air. Finally, there is also no restriction whatsoever with regard to the duration of the calcination step in the optional step (vi). Thus, the duration of the calcination in the optional calcination step in (vi) may, for example, be 0.5 to 20 hours, preference being given to a duration of 1 to 15 h, further preferably of 2 to 10 h, further preferably of 3 to 7 h, and particular preference to a duration of 4 to 5 h. Thus, according to the present invention, preference is given to embodiments of the process for preparing the catalyst, and especially the catalyst according to one of the particular or preferred embodiments thereof, in which the calcining in (vi) is effected at a temperature in the range from 300 to 850° C., preferably from 400 to 750° C., further preferably from 450 to 700° C., further preferably from 500 to 650° C., further preferably from 530 to 600° C., and further preferably from 540 to 560° C.

In step (ii) of the preferred process for preparing the catalyst, the one or more zeolites of the MFI. MEL and/or MWW structure type are first mixed with one or more solvents. According to the present invention, there is no restriction whatsoever in step (ii) with regard to the type and/or number of solvents used for this purpose. Thus, it is possible in principle to use any suitable solvent or solvent mixture in step (ii), provided that it is suitable for enabling homogenization in step (iii) and the coating in step (iv). For example, it is possible in step (ii) to use one or more solvents selected from the group consisting of alcohols, water, mixtures of two or more alcohols and mixtures of water and one or more alcohols. In preferred embodiments of the present invention, the one or more solvents used in (ii) are selected from the group consisting of $(C_1-C_6)$-alcohols, water, mixtures of two or more $(C_1-C_6)$-alcohols and mixtures of water and one or more $(C_1-C_6)$-alcohols, the one or more solvents further preferably being selected from the group consisting of $(C_1-C_6)$-alcohols, water, mixtures of two or more $(C_1-C_4)$-alcohols and mixtures of water and one or more $(C_1-C_4)$-alcohols. In further preferred embodiments, the one or more solvents in step (ii) are selected from the group consisting of methanol, ethanol, n-propanol, isopropanol, water and mixtures of two or more thereof, further preferably from the group consisting of methanol, ethanol, water and mixtures of two or more thereof, the solvent even further preferably being water, preferably distilled water.

Thus, according to the present invention, preference is given to embodiments of the process for preparing the catalyst, and especially the catalyst according to one of the particular or preferred embodiments thereof, in which the mixture prepared in (ii) comprises one or more solvents selected from the group consisting of alcohols, water, mixtures of two or more alcohols, and mixtures of water and one or more alcohols, preferably from the group consisting of $(C_1-C_6)$ alcohols, water, mixtures of two or more $(C_1-C_6)$ alcohols, and mixtures of water and one or more $(C_1-C_6)$ alcohols, further preferably $(C_1-C_4)$ alcohols, water, mixtures of two or more $(C_1-C_4)$ alcohols, and mixtures of water of one or more $(C_1-C_4)$ alcohols, further preferably consisting of methanol, ethanol, n-propanol, isopropanol, water and mixtures of two or more thereof, further preferably consisting of methanol, ethanol, water and mixtures of two or more thereof, the solvent further preferably being water, preferably distilled water.

With respect to the solids concentration of the mixture provided in (ii), according to the present invention, there are no particular restrictions whatsoever, provided that homogenizing of the mixture in step (iii) and the use of the homogenized mixture obtained in (vi) for the coating in (iv) are possible. Thus, the solids concentration of the mixture provided in (ii) may, for example, be in the range of 10-75% by weight, the solids concentration according to the present invention preferably being in the range of 15-65% by weight and further preferably in the range of 20-60% by weight and further preferably being in the range of 25-55% by weight and further preferably in the range of 30-50% by weight. In particularly preferred embodiments of the process according to the invention for preparing a catalyst, the solids concentration of the mixture provided in (v) is in the range of 35-45% by weight.

Thus, according to the present invention, preference is given to embodiments of the process for preparing the catalyst, and especially the catalyst according to one of the particular or preferred embodiments thereof, in which the solids concentration of the mixture prepared in (ii) is in the range from 10 to 75% by weight, preferably from 15 to 65% by weight, further preferably from 20 to 60% by weight, further preferably from 25 to 55% by weight, further preferably from 30 to 50% by weight, and further preferably from 35 to 45% by weight.

With regard to the homogenizing in step (iii) too, according to the present invention, there is no particular restriction whatsoever, and so it is possible to select any conceivable procedure in order to obtain a homogeneous mixture of the mixture prepared in step (ii), for which purpose it is possible to use, for example, one or more processes selected from the group consisting of stirring, kneading, agitating, vibration, or a combination of two or more thereof. According to the present invention, the mixture prepared in step (ii) is preferably homogenized by stirring and/or by vibration in step (iii), the homogenization in step (iii) further preferably being effected by vibration, preferably by means of ultrasound, for example by use of an ultrasound bath into which the mixture to be homogenized is introduced.

Thus, according to the present invention, preference is given to embodiments of the process for preparing the catalyst, and especially the catalyst according to one of the particular or preferred embodiments thereof, in which the homogenizing in (iii) is effected by stirring, kneading, agitating, vibration or combinations of two or more thereof, preferably by stirring and/or vibration, further preferably by vibration, and further preferably by means of ultrasound.

With regard to the coating of the support substrate in step (iv) of the process according to the invention, there is in principle no restriction whatsoever with respect to the performance thereof, provided that a corresponding layer is formed thereby at least partially on the support substrate. Thus, any suitable form of coating or of layer formation can be employed in the process according to the invention for preparing the inventive catalyst, the coating in step (iv) preferably being effected by spray coating and/or wash coating. In particularly preferred embodiments of the process according to the invention, the coating in step (iv) is effected by wash coating, the wash coating preferably being effected by dip coating. Such a preferred dip coating operation is effected, for example, by dipping the support substrate once or more than once into the mixture prepared in step (ii) and homogenized in step (iii), and, according to the present invention, the dip coating is preferably followed by a treatment to remove excess mixture from the support substrate. In preferred embodiments of dip coating, in which the substrate is dipped repeatedly into the mixture prepared in step (ii) and homogenized in step (iii), the further preferred treatment for removal of excess mixture can in principle be effected after the repeated dipping and/or between two or more dipping steps, each dipping step preferably being followed by removal of excess mixture by a suitable treatment of the coated support substrate. More preferably, however, according to the present invention, one dipping step into the mixture prepared in step (ii) and homogenized in step (iii) is performed, followed by a corresponding treatment for removal of excess mixture. With regard to the particularly preferred removal of excess mixture according to the particular embodiments of the present process, in which dip coating is performed in step (iv), there is in principle no restriction whatsoever with respect to the way in which excess mixture is removed. Thus, a removal can be achieved, for example, by suitable hanging of the coated support substrate and/or leaving it to stand, and/or directly or indirectly by mechanical or other action, for example by mechanical stripping and/or by removal with a suitable gas blower and/or by suitable application of centripetal forces, for example by means of centrifugal forces directed in a suitable manner. According to the present invention, however, particular preference is given to removing excess mixture by means of a gas blower, more preferably with the aid of compressed air by suitable extractive blowing of the excess mixture.

Thus, according to the present invention, preference is given to embodiments of the process for preparing the catalyst, and especially the catalyst according to one of the particular or preferred embodiments thereof, in which the coating in (iv) is effected by spray coating and/or wash coating, preferably by wash coating, the wash coating preferably being effected by dip coating, which is preferably followed by a treatment for removal of excess mixture, the removal of excess mixture preferably being effected at least partly with compressed air.

In the process according to the invention, according to the present invention, it is possible in principle to provide the support substrate with a plurality of layers of the same and/or different composition, especially with respect to the one or more zeolites of the MFI. MEL and/or MWW structure type. Thus, preference is given to, embodiments of the process according to the invention for preparing a catalyst according to the present invention in which step (iv) is repeated once or more than once, step (v) and/or step (vi) and preferably both step (v) and step (vi) preferably being executed between the repetitions. In such preferred embodiments of the process according to the invention in which two or more layers of different composition, especially with respect to the one or more zeolites, are applied to the support substrate, steps (ii) and (iii) are also repeated correspondingly in the case of preparation of the different compositions of the mixture in step (ii), and this may relate not just to the chemical composition but also to further properties of the mixture, for example the average particle size of the one or more zeolites of the MFI. MEL and/or MWW structure type. In particularly preferred embodiments of the process according to the invention, steps (iv) and (v) and/or (vi), preferably steps (iv)-(vi), are repeated once or more than once, in order to achieve multiple coating of the support substrate with a mixture prepared in step (ii) and homogenized in step (iii).

With regard to the number of repetitions which, in the preferred embodiments of the process according to the invention for preparing a catalyst according to the present invention, there is no restriction in principle, and the steps in the repetitions of the particular and preferred embodiments of the process according to the invention are preferably repeated once to five times, further preferably once to four times, further preferably once to three times and further preferably once or twice.

Thus, according to the present invention, preference is given to embodiments of the process for preparing the catalyst, and especially the catalyst according to one of the particular or preferred embodiments thereof, in which step (iv) is repeated once or more than once, preferably steps (iv) and (v), further preferably steps (iv) to (vi), and the steps are preferably repeated once to five times, further preferably once to four times, further preferably once to three times and further preferably once or twice.

According to the particularly preferred embodiments of the present invention in which the one or more zeolites of the MFI, MEL and/or MWW structure type may each be present in the catalyst in the H form thereof, these may, in correspondingly preferred embodiments of the process for preparing the catalyst, either be provided in the H form in step (i) and/or converted to the H form during the process by suitable treatment and especially by ion exchange. In the preferred embodiments of the process for preparing the catalyst according to which the one or more zeolites are converted to the H form during the preparation, there are no particular restrictions in principle with respect to the manner in which this is conducted, the conversion of the one or more zeolites preferably being effected by ion exchange. The one or more zeolites can thus also be converted to the H form at any suitable point in the process, this preferably being performed after the preparation of the mixture in (ii) or after the coating and optional drying and/or calcining, preferably after the drying of the coated support substrate in (v) and more preferably after the calcining of the coated support substrate in (vi), the conversion to the H form preferably being effected on the dried and calcined coated support substrate.

With respect to the preferred embodiments of the process for preparing the catalyst according to which the conversion of the one or more zeolites of the MFI, MEL and/or MWW structure type to the H form is effected over one or more ion exchange steps, there are again no particular restrictions with respect to the manner in which this is conducted, provided that at least some of the counterions to the zeolite skeleton are exchanged by $H^+$ ions. In preferred embodiments, for the purpose of ion exchange, the one or more zeolites are contacted with a solution of a protonated volatile base, preferably of a protonated volatile amine, more preferably with an ammonium salt solution, or alternatively with an acid and preferably with an aqueous acid solution, preferably with an aqueous solution of a mineral acid. With respect to the ammonium salts which are preferably used, there is no general restriction, provided that the exchange of at least some of the counterions present in the one or more zeolites for ammonium can be accomplished. For example, it is possible for this purpose to use one or more ammonium salts selected from the group consisting of $NH_4NO_3$, $(NH_4)_2SO_4$ and mixtures of two or more thereof. The same applies correspondingly with respect to the acids and especially the mineral acids which can be used for the purpose of ion exchange, provided that the exchange of at least some of the counterions present in the one or more zeolites for $H^+$ can be accomplished. Thus, it is possible to use, for example, solutions of the mineral acids $HNO_3$, $HCl$, $H_2SO_4$, and also mixtures of two or more thereof for the ion exchange. With respect to the concentration of the solutions of protonated volatile bases or of acids used for the preferred ion exchange, there is no particular restriction whatsoever, provided that at least some of the counterions of the zeolite skeleton can be exchanged, and, in the case of use of one or more acids, that the pH of the solution does not lead to any significant dissolution of the zeolite skeleton. Thus, it is possible to use, for example, solutions of the salts or of the acids having a concentration of 1 to 50% by weight, preference being given to using concentrations of 5 to 30% by weight and more preferably of 10 to 25% by weight for the ion exchange. The same applies correspondingly with respect to the weight ratio of salt or acid solution to the one or more zeolites which are ion-exchanged. Thus, the weight ratio of the solution used for the ion exchange to the one or more zeolites may, for example, be in the range from 1 to 20, the weight ratio preferably being in the range from 2 to 10 and further preferably in the range from 4 to 7.

The ion exchange may in principle here precede the provision of the one or more zeolites in step (i), or follow one or more of the steps of the preferred process for preparing the catalyst, an ion exchange preferably being performed prior to the provision in step (i) and/or after the coating and optional drying and/or calcining, preferably after the drying of the coated support substrate in (v) and more preferably after the calcining of the coated support substrate in (vi). In the preferred embodiments of the preparation of the catalyst used in the process according to the invention in which a step of ion exchange with a protonated volatile base, and preferably with a protonated volatile amine, more preferably with ammonium, is performed after the calcining in (vi), it is further preferred that, after the ion exchange and an optional wash step and/or after an optional drying step, a further calcining step is performed in order to remove the volatile base and more preferably ammonia completely from the ion-exchanged zeolite.

EXAMPLES

Comparative Example 1: Preparation of an Extrudate Comprising ZSM-5

380 g of H-ZSM-5 (ZEO-cat PZ2-100 H from Zeochem) with Si/Al=50 were mixed with 329 g of pseudoboehmite (Pural SB; Sasol), admixed with 10 g of formic acid in 50 ml of water and processed with 300 ml of water in a kneader to give a homogeneous material. The starting weights were selected such that the zeolite/binder ratio in the calcined extrudate corresponds to 60:40. This kneaded material was pushed with the aid of an extrudate press at approx. 100 bar through a 2.5 mm die. The extrudates were subsequently dried in a drying cabinet at 120° C. for 16 h and (after heating time 4 h) calcined in a muffle furnace at 500° C. for 4 h. Thereafter, the extrudates were processed in a sieving machine with 2 steel balls (diameter approx. 2 cm, 258 g/ball) to give 1.6-2.0 mm spall.

Example 1: Preparation of a Support Coated with ZSM-5

An aqueous suspension having a solids concentration of 40% by weight of H-ZSM-5 zeolite (ZEO-cat PZ2-100 H from Zeochem) with Si/Al=50 was prepared and homogenized in an ultrasound bath. Cylindrical honeycomb pieces of cordierite (900 cpsi, diameter 0.9 cm, length=11 cm) were dipped into this suspension and then blown dry with compressed air. The coated supports were then dried at 110° C. for 1 h and subsequently calcined at 550° C. for 3 h. The coating step was repeated until a loading of 0.5 g of zeolite per honeycomb piece (0.071 g/cm$^3$) was attained.

Example 2: Methanol-to-Olefin Process with Preceding Conversion of Methanol to Dimethyl Ether 2 g of the catalyst prepared according to comparative example 1 were mixed with 24 g of silicon carbide and installed in a continuous, electrically heated tubular reactor, such that the bed in the reactor has a length of 30 cm and a diameter of 12 mm. For the tests using the catalyst prepared according to example 1, two of the coated honeycomb bodies were installed in the reactor and sealed at the tube wall with glass fiber cord.

Upstream of the test reactor, methanol vapor was produced to give a gas stream comprising 75% by volume of methanol and 25% by volume of $N_2$, which was converted to dimethyl ether by means of a preliminary reactor charged with 34 ml of alumina spall at 275° C. and an (absolute)

pressure of 1-2 bar. The stream comprising dimethyl ether was then passed into the tubular reactor, and converted therein at a temperature of 450 to 500° C., a WHSV (=weight hourly space velocity, is calculated as the ratio of oxygenate reactant stream in kg/h to the amount of zeolite in the reactor in kg) of 7 or 10 h$^{-1}$ based on, methanol and an (absolute) pressure of 1 to 2 bar, and the reaction parameters were maintained over the entire run time. Downstream of the tubular reactor, the gaseous product mixture was analyzed by on-line chromatography.

On completion of one cycle with the catalyst according to example 1, the catalyst was deinstalled and calcined in a muffle furnace at 500° C. in an air atmosphere for 5 h, in the course of which the coke was almost completely incinerated. The regenerated catalyst was subsequently used again in the test reactor under the same conditions as the fresh catalyst from example 1.

The results achieved in the MTO process for the catalysts according to comparative example 1 and according to example 1 (before and after the regeneration of the catalyst) with respect to the selectivities are shown in table 1, these reproducing the average selectivities during the run time of the catalyst in which the conversion of methanol was 95% or more.

TABLE 1

Average selectivities of a cycle (methanol conversion of >95%).

| | Comparative example 1 | Example 1 | Example 1 after regeneration |
|---|---|---|---|
| Service life [h] | 33 | 53 | 68 |
| WHSV [h$^{-1}$] | 10 | 7 | 7 |
| MeOH load per cycle [kg$_{MeOH}$ · kg$_{zeolite}^{-1}$] | 330 | 371 | 476 |
| Selectivity [%]: | | | |
| ethylene | 9 | 8 | 8 |
| propylene | 24 | 19 | 25 |
| butylene | 15 | 17 | 20 |
| C$_4$ paraffins | 10 | 12 | 9 |
| C$_{5+}$ (mixture) | 16 | 18 | 20 |
| aromatics | 19 | 18 | 13 |
| C$_1$-C$_3$ paraffins | 7 | 8 | 5 |

As can be inferred from the values in table 1, it has been found that, surprisingly, the specific use of a zeolite which has been applied to a support substrate in an MTO process with a preliminary reaction of methanol to give dimethyl ether enables a surprisingly long service life or an unexpectedly high methanol load per cycle of the catalyst at which a methanol conversion of more than 95% can be maintained. AU the more surprising is the fact that the regeneration of the catalyst by calcination led to a further considerable gain in service life (see example 1 after regeneration in table 1). Furthermore, the results of the reaction for the regenerated catalyst show that the latter also has a further gain in selectivity for butylene compared to the fresh catalyst, and also exhibits a selectivity for propylene which is higher than the selectivity achieved for the comparative example. Thus, the present invention provides a process for the conversion of ethers to olefins which, as shown by the test results in the MTO process using the catalyst according to example 1, enables much longer service lives compared to such a process which uses a catalyst in the form of an extrudate (see results with the catalyst from comparative example 1). Furthermore, the process surprisingly achieves an additional gain toward longer service lives, and also unexpectedly higher C$_3$ and C$_4$ selectivities compared to the comparative example after the regeneration of the catalyst by calcination.

The invention claimed is:

1. A process for converting oxygenates to olefins, the process comprising:
converting one or more C$_1$-C$_4$ alcohols or mixtures of two or more thereof to one or more ethers in a dehydrogenation reactor to provide a gas stream comprising the one or more ethers and water;
contacting a catalyst, which includes a support substrate and a catalytic layer applied to the substrate, the layer comprising one or more zeolites of the MFI, MEL, or MWW structure type or any one mixture thereof, with the gas stream and further comprising
calcining the catalyst only in air atmosphere to provide a regenerated catalyst,
providing the gas stream, and
contacting the regenerated catalyst with the gas stream wherein selectivity of C$_3$ and C$_4$ is increased after being subjected to the regeneration of the catalyst.

2. The process according to claim 1, wherein the support substrate is selected from the group consisting of granules, pellets, meshes, rings, spheres, cylinders, hollow cylinders, monoliths and mixtures thereof, and any one combination of two or more thereof.

3. The process according to claim 1, wherein the one or more monoliths are selected from the group consisting of honeycombs, braids, foams and combinations of two or more thereof.

4. The process according to claim 1, wherein the support substrate is selected from a ceramic substrate, metallic substrate, or mixed a ceramic/metallic substrate.

5. The process according to claim 1, wherein the one or more zeolites includes the MFI structure type.

6. The process according to claim 1, wherein the catalyst comprises the one or more zeolites includes a total loading of 0.005 to 1 g/cm$^3$ based on the volume of the coated support substrate.

7. The process according to claim 1, wherein the one or more ethers are selected from di(C$_1$-C$_3$)alkyl ethers, and the ethers are present in a range from 30% to 100% by volume, based on the total volume of the gas stream.

8. The process according to claim 7, wherein water is present in the gas stream in a range from 5 to 60% by volume, based on the total volume of the gas stream.

9. The process according to claim 7, wherein the contacting of the catalyst with the gas stream is conducted at a temperature in range from 200° to 700° C., and at a pressure in a range from 0.1 to 10 bar.

10. The process according to claim 9, wherein the contacting of the catalyst with the gas stream is a continuous process with a space velocity in a range from 0.5 to 50 h$^{-1}$.

11. The process according to claim 10, wherein the catalyst has a service life without interruption in a range from 15 to 200 h.

12. The process according to claim 1, wherein the calcination is performed at a temperature in a range from 200° to 1100° C.

13. The process according to claim 12, wherein the calcination is performed for a period of 0.25 to 30 h.

14. The process according to claim 12, wherein the catalyst can be regenerated from 10 to 1000 times following each process cycle.

15. The process according to claim 1, wherein the catalyst is prepared by a process comprising (i) providing the support substrate and the one or more zeolites of the MFI, MEL, or MWW structure type, or any one mixture thereof;
(ii) preparing a mixture comprising the one or more zeolites and one or more solvents;
(iii) homogenizing the mixture obtained in step (ii);
(iv) coating the support substrate with the homogenized mixture obtained in step (iii);
(v) optionally drying the coated support substrate obtained in step (iv); and
(vi) optionally calcining the coated support substrate obtained in step (iv) or step (v).

16. The process according to claim 15, wherein the drying in step (v) is conducted at a temperature in a range from 50° to 220° C., or the calcining in step (vi) is conducted at a temperature in a range from 300° to 850° C.

17. The process according to claim 15, wherein the one or more solvents are selected from the group consisting of alcohols, water, mixtures of two or more alcohols, and mixtures of water and one or more alcohols.

18. The process according to claim 15, wherein the mixture prepared in step (ii) includes a solids concentration in a range from 10% to 75% by weight.

19. The process according to claim 15, wherein the homogenizing in step (iii) is conducted by stirring, kneading, agitating, vibrating or any one combination thereof, and the coating in step (iv) is conducted by spray coating, wash coating or a combination of the two.

20. The process according to claim 15, wherein the step (iv) is repeated once or more than once.

21. A process for converting oxygenates to olefins, the process comprising:
converting one or more $C_1$-$C_4$ alcohols or mixtures of two or more thereof to one or more ethers in a dehydrogenation reactor to provide a gas stream comprising the one or more ethers and water;
contacting a catalyst, which includes a support substrate and a catalytic layer applied to the substrate, the layer comprising one or more zeolites of the MFI, MEL, or MWW structure type or any one mixture thereof, with the gas stream and further comprises the further steps of
(3) calcining the catalyst for regeneration only in air atmosphere;
(4) providing a gas stream comprising one or more ethers;
(5) contacting the gas stream provided in (4) with the regenerated catalyst.

* * * * *